United States Patent [19]

Irwin

[11] Plant 4,068

[45] June 28, 1977

[54] KALANCHOE PLANT

[76] Inventor: Lawrence T. Irwin, P. O. Box 657, Canyon, Tex. 79015

[21] Appl. No.: 693,883

[22] Filed: June 7, 1976

[51] Int. Cl.[2] ..... A01H 5/00

[52] U.S. Cl. ..... Plt./68

[58] Field of Search ..... Plt./68

*Primary Examiner*—Robert E. Bagwill
*Attorney, Agent, or Firm*—Frank B. Robb

EXEMPLARY CLAIM

A new and distinct variety of Kalanchoe plant, substantially as herein shown and described, characterized particularly as to novelty by the unique combination of a tall, upright, vigorous habit, growing 16 inches to 20 inches in height; the very large flowers of about 2 cm diameter; the unique scarlet color of the flowers with a definite yellow eye (4); profusion of flowers carried on sturdy stems 4 inches to 6 inches above the foliage; the medium large size flexible foliage of fern green color; and the adaptability to year round flowering with photoperiod manipulation.

1 Drawing Figure

1

The present invention relates to a new and distinct variety of Kalanchoe plant which was originated by me by crossing the Kalanchoe variety known as "Exotic" (U.S. Plant Pat. No. 3,149) which I identify as the seed parent, with an unpatented variety which I designate as "Ramona", this latter parent being the pollen parent. As a result of this breeding which is one part of a concentrated series of breeding and development of Kalanchoe plants which I have carried on for some time, I have produced a new and improved Kalanchoe variety, this one being distinguished among others and from its parents as well as from numerous varieties of Kalanchoes of which I am aware, as evidenced by the following unique combination of principal characteristics which are outstanding in the new variety and which make it a valuable addition to the line of Kalanchoe varieties that are presently commercially available among those which I have previously developed:

1. Upright, vigorous growth, and tall habit, reaching 16 inches to 20 inches in height;
2. The very large eyed flowers, the flower diameter being on the order of 2 cm;
3. The unique scarlet color of the flowers and the contrasting eye therein;
4. The profusion of the flowers carried on a sturdy stem 4 inches to 6 inches above the foliage;
5. The medium large size flexible foliage of fern green color; and
6. The year round adaptability to flowering with photoperiod manipulation.

I have carried on the asexual reproduction of my new Kalanchoe variety by means of cuttings in the program of hybridization which I am carrying on presently, performed by me in my greenhouses located in Canyon, Tex., shows that the foregoing characteristics and distinctions come true and are established and transmitted through succeeding propagation.

When comparison is had of the outstanding features of my new variety of Kalanchoe in comparison with comparable features of the parent varieties, it is notable that my new variety is taller and more upright and vigorous than either parent.

Further, the larger flowers of my new variety are of greater size than either parent likewise.

The unique scarlet colored flower with its distinctive yellow eye is additionally substantially different from either parent.

2

Finally, the flowers are developed at about the same time as the variety "Exotic" and about two weeks sooner than those of "Ramona".

The accompanying drawing shows a typical blooming plant of my new variety, as well as a close-up view of the flowers as depicted in color as nearly true as it is possible to make the same in a color illustration of this character.

There follows a description of my new variety, with color terminology in accordance with Maerz and Paul Dictionary of Color as contained in Exotica No. 2 by A. B. Graf, the readings being effected in fiberglass greenhouses, except where general color terms which have ordinary dictionary significance will or could be applicable and are used incidentally:

Parentage: Seedling.

*Seed parent.*—"Exotic" (U.S. Plant Pat. No. 3,149).

*Pollen parent.*—"Ramona" an unpatented variety.

Propagation: Holds its distinguishing characteristics through succeeding propagations by cuttings.

Locality where grown and observed: Canyon, Tex.

Plant:

*Form.*—Tall; upright.

*Growth habit.*—Much branched; upright; tall, about 16 inches to 20 inches in height.

*Rooting habit.*—Coordinate; roots easily from any part of the stem forming a fibrous root system.

*Blooming habit.*—A short day plant, flowering naturally approximately Dec. 18.

*Blooming season.*—Due to its short day response to flowering, this new variety can be brought into bloom the year around by appropriate photoperiod manipulation; blooms in about 12 weeks.

Foliage:

*Size.*—Large.

*Quantity.*—Abundant.

*Color.*—New foliage — Upper side — (83) Fern Green; Under side — (83−). Old foliage — Upper side — (83+); Under side — (83). Texture — Upper side — Glossy and smooth; Under side — Smooth.

Disease Resistance: Comparable to that of other newer hybrids which are more resistant than standard varieties, as determined by comparison with such other varieties grown in the same greenhouses under the same conditions at Canyon, Tex.

Flowers: Pistillate; staminate; perfect complete.

*Size.*—Large. Diameter — 2 cm. Depth — 1.4 cm.

*Petals.*—Length — 0.8 cm. Width — 0.9 cm.

*Form.*—Umbel.

*Color.*—Upper side — New flowers — Scarlet (25); Old flowers — Maintain same color. Under side — New flowers — (29-30) range of color. Throat of corolla — Has a very distinctive yellow eye (4)

*Blooming period.*—From 4 to 5 weeks.

Fruit: None.

Hardiness: Grown in the greenhouse 50° F to 100° F without any problem. Is not winter hardy in temperate climates.

General observations: The new variety has all the desirable qualities of a good pot plant. Its large flower is larger than any known commercially grown Kalanchoe. Its flower size, vigor, distinctive color and yellow eye make it a unique Kalanchoe variety among other Kalanchoe varieties.

I claim:

1. A new and distinct variety of Kalanchoe plant, substantially as herein shown and described, characterized particularly as to novelty by the unique combination of a tall, upright, vigorous habit, growing 16 inches to 20 inches in height; the very large flowers of about 2 cm diameter; the unique scarlet color of the flowers with a definite yellow eye (4); profusion of flowers carried on sturdy stems 4 inches to 6 inches above the foliage; the medium large size flexible foliage of Fern Green color; and the adaptability to year round flowering with photoperiod manipulation.

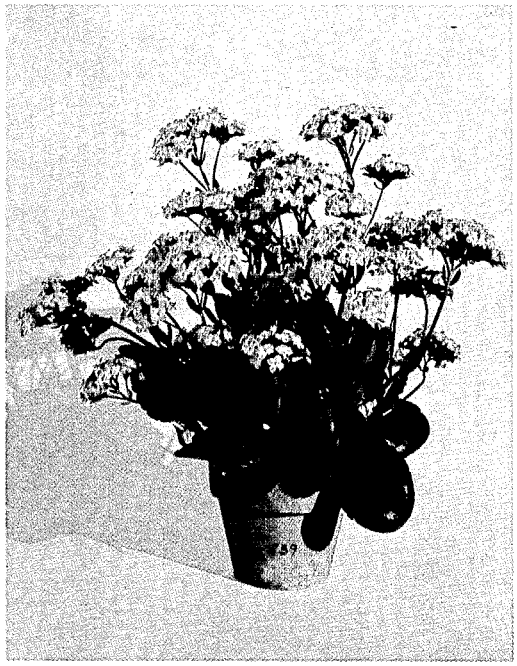
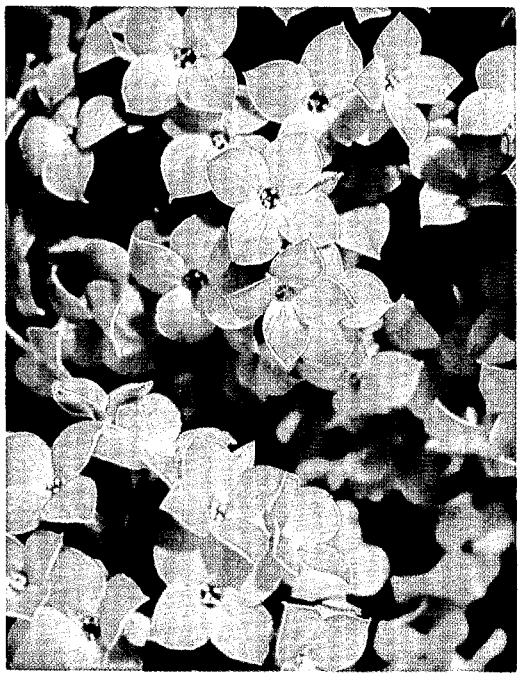

* * * * *